(12) United States Patent
Schwartz et al.

(10) Patent No.: US 9,173,826 B2
(45) Date of Patent: *Nov. 3, 2015

(54) POROUS, DISSOLVABLE SOLID SUBSTRATE AND SURFACE RESIDENT COATING COMPRISING A ZYNC PYRITHIONE

(75) Inventors: James Robert Schwartz, West Chester, OH (US); Robert Wayne Glenn, Jr., Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/028,846

(22) Filed: Feb. 16, 2011

(65) Prior Publication Data

US 2011/0200649 A1    Aug. 18, 2011

Related U.S. Application Data

(60) Provisional application No. 61/305,127, filed on Feb. 16, 2010.

(51) Int. Cl.
| | |
|---|---|
| *A61K 33/32* | (2006.01) |
| *A61K 8/49* | (2006.01) |
| *A61K 8/02* | (2006.01) |
| *A61K 8/04* | (2006.01) |
| *A61Q 9/02* | (2006.01) |
| *A61Q 19/00* | (2006.01) |
| *A61Q 9/04* | (2006.01) |

(52) U.S. Cl.
CPC ............ *A61K 8/4933* (2013.01); *A61K 8/0208* (2013.01); *A61K 8/046* (2013.01); *A61Q 9/02* (2013.01); *A61Q 19/00* (2013.01); *A61K 2800/242* (2013.01); *A61Q 9/04* (2013.01)

(58) Field of Classification Search
None
See application file for complete search history.

(56) References Cited

U.S. PATENT DOCUMENTS

| | | |
|---|---|---|
| 2,356,168 A | 8/1941 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer et al. |
| 2,658,072 A | 11/1953 | Kosmin |

(Continued)

FOREIGN PATENT DOCUMENTS

| | | |
|---|---|---|
| CN | 1138091 | 12/1996 |
| CN | 1219388 A | 6/1999 |

(Continued)

OTHER PUBLICATIONS

International Search Report PCT/US2011/025033 dated Jul. 13, 2011 including the Written Opinion of the International Searching Authority, 8 pages.

(Continued)

*Primary Examiner* — Abigail Fisher
*Assistant Examiner* — Daniel L Branson

(57) ABSTRACT

The present invention relates to personal care compositions, especially those shave preparation article and skin care articles which are in the form of a porous dissolvable solid substrate having a surface resident coating comprising at least one skin treatment active. The present invention can deliver a consumer benefit as well as allow for separation of any incompatible actives in the substrate versus the coating.

19 Claims, 2 Drawing Sheets

(56) References Cited

U.S. PATENT DOCUMENTS

| | | |
|---|---|---|
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau et al. |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs et al. |
| 4,089,945 A | 5/1978 | Brinkman |
| 4,149,551 A | 4/1979 | Benjamin et al. |
| 4,196,190 A | 4/1980 | Gehman |
| 4,197,865 A | 4/1980 | Jacquet |
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,565,693 A | 1/1986 | Marschner |
| 4,663,158 A | 5/1987 | Wolfram |
| 4,708,863 A | 11/1987 | Bews et al. |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard et al. |
| 5,055,384 A | 10/1991 | Kuhnert |
| 5,061,481 A | 10/1991 | Suzuki |
| 5,062,889 A | 11/1991 | Hohl et al. |
| 5,094,853 A | 3/1992 | Hagarty |
| 5,100,657 A | 3/1992 | Ansher-Jackson |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |
| 5,220,033 A | 6/1993 | Kamei et al. |
| 5,261,426 A | 11/1993 | Kellett et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson et al. |
| 5,476,597 A | 12/1995 | Sakata et al. |
| 5,518,774 A * | 5/1996 | Kappock et al. ............ 427/384 |
| 5,580,481 A | 12/1996 | Sakata et al. |
| 5,582,786 A | 12/1996 | Brunskill |
| 5,660,845 A | 8/1997 | Trinh |
| 5,672,576 A | 9/1997 | Behrens et al. |
| 5,674,478 A | 10/1997 | Dodd |
| 5,750,122 A | 5/1998 | Evans |
| 5,780,047 A | 7/1998 | Kamiya et al. |
| 5,955,419 A | 9/1999 | Barket, Jr. |
| 5,976,454 A | 11/1999 | Sterzel et al. |
| 6,010,719 A | 1/2000 | Remon |
| 6,015,547 A | 1/2000 | Yam |
| 6,096,297 A | 8/2000 | Jones et al. |
| 6,106,849 A | 8/2000 | Malkan et al. |
| 6,177,391 B1 | 1/2001 | Zafar |
| 6,200,949 B1 | 3/2001 | Reijmer |
| 6,365,142 B1 | 4/2002 | Tamura |
| 6,458,754 B1 | 10/2002 | Velaquez |
| 6,503,521 B1 | 1/2003 | Atis et al. |
| 6,525,034 B2 | 2/2003 | Dalrymple et al. |
| 6,540,791 B1 * | 4/2003 | Dias ................ 8/111 |
| 6,790,814 B1 | 9/2004 | Marin |
| 6,800,295 B2 | 10/2004 | Fox |
| 6,808,375 B2 | 10/2004 | Klotzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,887,859 B2 | 5/2005 | Clapp et al. |
| 6,943,200 B1 | 9/2005 | Corrand et al. |
| 7,015,181 B2 | 3/2006 | Lambino |
| 7,208,460 B2 | 4/2007 | Shefer et al. |
| 7,285,520 B2 | 10/2007 | Krzysik et al. |
| 7,381,415 B2 | 6/2008 | Yokoyama et al. |
| 7,387,787 B2 | 6/2008 | Fox |
| 7,846,462 B2 | 12/2010 | Spadini et al. |
| 7,901,696 B2 | 3/2011 | Eknoian |
| 8,119,168 B2 | 2/2012 | Johnson et al. |
| 8,197,830 B2 | 6/2012 | Helfman et al. |
| 8,268,764 B2 | 9/2012 | Glenn, Jr. et al. |
| 8,273,333 B2 | 9/2012 | Glenn et al. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn et al. |
| 8,349,787 B2 | 1/2013 | Glenn et al. |
| 8,415,287 B2 | 4/2013 | Glenn, Jr. et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| 8,476,211 B2 | 7/2013 | Glenn, Jr. et al. |
| 8,491,877 B2 | 7/2013 | Schwartz et al. |
| 8,546,640 B2 | 10/2013 | Popovsky et al. |
| 8,978,666 B2 | 3/2015 | Schwartz |
| 2002/0064510 A1 | 5/2002 | Dalrymple |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada |
| 2002/0187181 A1 | 12/2002 | Godbey et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Mino |
| 2004/0048759 A1 | 3/2004 | Ribble et al. |
| 2004/0053808 A1 | 3/2004 | Raehse et al. |
| 2004/0071742 A1 | 4/2004 | Popplewell |
| 2004/0108615 A1 | 6/2004 | Foley |
| 2004/0110656 A1 | 6/2004 | Casey |
| 2004/0126585 A1 | 7/2004 | Kerins et al. |
| 2004/0161435 A1 | 8/2004 | Gupta |
| 2004/0175404 A1 | 9/2004 | Shefer |
| 2004/0191331 A1 | 9/2004 | Schwartz et al. |
| 2004/0202632 A1 | 10/2004 | Gott |
| 2004/0206270 A1 | 10/2004 | Vanmaele |
| 2004/0242097 A1 | 12/2004 | Hasenoehrl et al. |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1 | 6/2005 | Gaserod et al. |
| 2005/0202984 A1 | 9/2005 | Schwartz et al. |
| 2005/0202992 A1 | 9/2005 | Portables |
| 2005/0220745 A1 | 10/2005 | Lu |
| 2005/0232954 A1 | 10/2005 | Yoshinari |
| 2005/0244352 A1 | 11/2005 | Lemoine et al. |

(56) References Cited

U.S. PATENT DOCUMENTS

| | | |
|---|---|---|
| 2005/0272836 A1 | 12/2005 | Yaginuma et al. |
| 2005/0287106 A1 | 12/2005 | Legandre |
| 2006/0002880 A1 | 1/2006 | Peffly |
| 2006/0013869 A1 | 1/2006 | Ignatious et al. |
| 2006/0024381 A1 | 2/2006 | Schwartz et al. |
| 2006/0052263 A1 | 3/2006 | Roreger |
| 2006/0228319 A1 | 10/2006 | Vona, Jr. et al. |
| 2007/0028939 A1 | 2/2007 | Mareri et al. |
| 2007/0128147 A1 | 6/2007 | Schwartz et al. |
| 2007/0149435 A1 | 6/2007 | Koenig |
| 2007/0190177 A1 | 8/2007 | Kling et al. |
| 2007/0225388 A1 | 9/2007 | Cooper et al. |
| 2008/0035174 A1 | 2/2008 | Aubrun-Sonneville et al. |
| 2008/0063618 A1 | 3/2008 | Johnson et al. |
| 2008/0083420 A1 | 4/2008 | Glenn et al. |
| 2008/0090939 A1 | 4/2008 | Netravali et al. |
| 2008/0131695 A1 | 6/2008 | Aouad |
| 2008/0138441 A1 | 6/2008 | Schwartz et al. |
| 2008/0138442 A1 | 6/2008 | Johnson et al. |
| 2008/0138492 A1 | 6/2008 | Cingotti |
| 2008/0152894 A1 | 6/2008 | Beihoffer et al. |
| 2008/0160093 A1 | 7/2008 | Schwartz et al. |
| 2008/0206355 A1 | 8/2008 | Schwartz et al. |
| 2008/0215023 A1 | 9/2008 | Scavone |
| 2008/0292669 A1 | 11/2008 | Deng et al. |
| 2008/0293839 A1 | 11/2008 | Stobby |
| 2009/0232873 A1 * | 9/2009 | Glenn et al. ............... 424/443 |
| 2010/0167971 A1 | 7/2010 | Glenn, Jr. |
| 2010/0173817 A1 | 7/2010 | Glenn, Jr. |
| 2010/0291165 A1 | 11/2010 | Glenn, Jr. |
| 2011/0023240 A1 | 2/2011 | Fossum |
| 2011/0027328 A1 | 2/2011 | Baig et al. |
| 2011/0028374 A1 | 2/2011 | Fossum |
| 2011/0182956 A1 | 7/2011 | Glenn, Jr. |
| 2011/0195098 A1 | 8/2011 | Glenn, Jr. |
| 2011/0197906 A1 | 8/2011 | Schwartz |
| 2011/0200650 A1 | 8/2011 | Schwartz |
| 2011/0201588 A1 | 8/2011 | Schwartz |
| 2011/0250256 A1 | 10/2011 | Hyun-Oh et al. |
| 2012/0021026 A1 | 1/2012 | Chhabra et al. |
| 2012/0270029 A1 | 10/2012 | Glenn, Jr. et al. |
| 2012/0321580 A1 | 12/2012 | Glenn et al. |
| 2013/0236520 A1 | 9/2013 | Popovsky et al. |
| 2013/0280200 A1 | 10/2013 | Schwartz |

FOREIGN PATENT DOCUMENTS

| | | | |
|---|---|---|---|
| CN | 1268558 | A | 10/2000 |
| CN | 1357613 | | 7/2002 |
| CN | 1530431 | | 9/2004 |
| CN | 1583991 | A | 2/2005 |
| DE | 19607851 | A1 | 9/1997 |
| DE | 10331767 | A1 | 2/2005 |
| EP | 27730 | A2 * | 4/1981 |
| EP | 0 468 564 | A2 | 1/1992 |
| EP | 609808 | A1 | 8/1994 |
| EP | 0858828 | A1 | 8/1998 |
| EP | 1160311 | B1 | 12/2001 |
| EP | 1217987 | B1 | 12/2004 |
| EP | 1958532 | A2 | 8/2008 |
| EP | 2085434 | A1 | 8/2009 |
| FR | 2871685 | A1 | 12/2005 |
| FR | 2886845 | A1 | 12/2006 |
| GB | 2235204 | A | 2/1991 |
| GB | 2355008 | A | 4/2001 |
| JP | 58021608 | | 2/1983 |
| JP | 58216109 | | 12/1983 |
| JP | 62-072609 | | 4/1987 |
| JP | 62-072610 | | 4/1987 |
| JP | 62-081432 | | 4/1987 |
| JP | 01313418 | | 12/1989 |
| JP | 5344873 | A | 12/1993 |
| JP | 6017083 | A | 1/1994 |
| JP | 07-53349 | | 2/1995 |
| JP | 7089852 | A | 4/1995 |
| JP | 1998325133 | A | 12/1996 |
| JP | 10251371 | A1 | 9/1998 |
| JP | 200373700 | A | 3/2003 |
| JP | 200382397 | | 3/2003 |
| JP | 2004345983 | A | 12/2004 |
| JP | 2005171063 | A | 6/2005 |
| JP | 2006-176675 | A | 7/2006 |
| JP | 2007197540 | A | 8/2007 |
| JP | 2007091954 | A | 12/2007 |
| KR | 2002-0003442 | | 1/2002 |
| WO | 94/14408 | A1 | 7/1994 |
| WO | 94/14409 | A1 | 7/1994 |
| WO | 95/14495 | A1 | 6/1995 |
| WO | 00/35413 | A1 | 6/2000 |
| WO | 01/19948 | A1 | 3/2001 |
| WO | 01/24770 | A1 | 4/2001 |
| WO | 01/25322 | A1 | 4/2001 |
| WO | 01/25393 | A1 | 4/2001 |
| WO | 01/54667 | A1 | 8/2001 |
| WO | 2004/032859 | A | 4/2004 |
| WO | 2004/041991 | A1 | 5/2004 |
| WO | 2005/003423 | A1 | 1/2005 |
| WO | 2006/110386 | A1 | 10/2006 |
| WO | 2007/033598 | A | 3/2007 |
| WO | 2007/093558 | A1 | 8/2007 |
| WO | 2009/019571 | A1 | 2/2009 |

OTHER PUBLICATIONS

ISR dated Jul. 20, 2012, PCT/US2012/032253, 5 pages.
All Office Actions, U.S. Appl. No. 12/424,812.
All Office Actions, U.S. Appl. No. 12/633,257.
All Office Actions, U.S. Appl. No. 12/633,301.
All Office Actions, U.S. Appl. No. 12/633,550.
All Office Actions, U.S. Appl. No. 12/633,335.
All Office Actions, U.S. Appl. No. 12/633,415.
All Office Actions, U.S. Appl. No. 12/633,572.
All Office Actions, U.S. Appl. No. 12/361,634.
All Office Actions, U.S. Appl. No. 12/962,846.
All Office Actions, U.S. Appl. No. 12/962,873.
All Office Actions, U.S. Appl. No. 12/962,888.
All Office Actions, U.S. Appl. No. 12/962,905.
All Office Actions, U.S. Appl. No. 13/173,639.
All Office Actions, U.S. Appl. No. 13/440,475.
All Office Actions, U.S. Appl. No. 13/597,539.
All Office Actions, U.S. Appl. No. 13/561,298.
All Office Actions, U.S. Appl No. 13/597,539.
Pure Soap Leafz: (Soap UNLTD, Netherlands, http://www.upandunder.co.uk/eshop/catalogue/testbs.asp?Manufacturer_ID=252&Activity_ID=33&Description_ID=157).
Dissolving Soap Strips (Ranir LLC, Michigan, www.ranir.com).
Japanese Paper Soap (http://www.wishingfish.com/papersoap.html).
Travelers Passport Paper Soap Sheets (http://www.weddingfavorsnow.com/index.asp?PageAction=VIEWPROD&ProdID=510).
ISR dated May 6, 2011, PCT/US2009/067130, 5 pages.
ISR dated May 4, 2011, PCT/US2009/067088, 5 pages.
ISR dated Jul. 19, 2011, PCT/US2009/067088, 7 pages.
ISR dated May 9, 2011, PCT/US2009/067132, 5 pages.
ISR dated Jul. 20, 2011, PCT/US2009/067131, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.
ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
ISR dated Jun. 7, 2013, PCT/US2010/059441, 9 pages.
ISR dated Feb. 20, 2013, PCT/US2011/042640, 12 pages.
C. D. Vaughan. Solubility, Effects in Product, Package, Penetration and Preservation, Cosmetics and Toiletries, vol. 103, Oct. 1988.

(56) References Cited

OTHER PUBLICATIONS

Encyclopedia of Polymer Science and Engineering, vol. 15, 2d ed., pp. 204 308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&Qs=0N&F=SPEC> [retrieved on Jul. 28, 2009].
M. K. Industires (Gujarat India, http://www.soapstrips.com).
Sanipro Sanitary Products (Italy, http://www.sanipro.it).
Adhesives Research (Pennsylvania, http://12.4.33.51/news/apresmed.htm).
Solublon (Toyohashi Japan, http://www.solublon.com).
SPI Pharma (Delaware, http://www.spipharma.com).
Wenda (China, http://www.wenda.com).
MOVA Pharmaceutical and Kosmos (USA, http://www.icon-pr.com/news/news_print.cfm?inv_id=266-1).
Cima Labs, Inc. (Minnesota, http://www.cimalabs.com/).
Cardinal Health (Dublin, Ohio, http://spd.cardinal.com/).
Le Laboratoire du Bain (France, http://www.labodubain.com/).
Amerilab Technologies, Inc. (Minnesota, http://www.amerilabtech.com/).
Meguiar's Car Wash Strips: (Meguiar's Inc. California, http://www.automotivedigest.com/view_art.asp?articlesID=12414).
T. Hildebrand, P. Ruegsegger. Quantification of bone microarchitecture with the structure model index. Comp Meth Biomech Biomed Eng 1997; 1:15-23.
Vesterby, A.; Star Volume In Bone Research A Histomorphometric Analysis of Trabecular Bone Structure Using Vertical Sections; Anat Rec.; Feb. 1993; 235(2):325-334.

\* cited by examiner

POROUS, DISSOLVABLE SOLID SUBSTRATE AND SURFACE RESIDENT COATING COMPRISING A ZYNC PYRITHIONE

CROSS REFERENCE TO RELATED APPLICATION

This application claims the benefit of U.S. Provisional Application No. 61/305,127, filed Feb. 16, 2010.

BACKGROUND OF THE INVENTION

Personal care compositions for use as shave preparations and/or skin care applications have traditionally been sold as a fluid (such as a liquid, gel, or foam) products or solid form (such as soap bars). Many actives which can be used in shave preparation and skin care applications, however, can be incompatible or generally not suited to be in the same fluid composition. Attempts to keep incompatible actives separate have been attempted but require separate packaging or multi-compartment packages which can involve complicated manufacture and filling processes. Solid form personal care compositions such as soap bars are useful and can be relatively inexpensive but they offer slow dissolution and sometimes limited lathering capabilities. Further, soap bars are often manufactured for multiple use and tend to become brittle and/or sticky as the bar gets worn down and repeatedly exposed to water—thus becoming non-user friendly. Despite the many attempts to commercialize personal care compositions, there remains a need for a personal care article that can be used as a shave preparation and/or a skin care application that can provide a high amount of lathering and moisturizing to the skin and can avoid incompatibilities in actives.

SUMMARY OF THE INVENTION

One aspect of the present invention provides for a personal care article comprising a first porous dissolvable solid substrate comprising from about 10% to about 75%, by weight of the first porous dissolvable solid substrate, of at least one surfactant; from about 10% to about 50%, by weight of the first porous dissolvable solid substrate, of a water-soluble polymer; from about 1% to about 30%, by weight of the first porous dissolvable solid substrate, of a plasticizer; and a surface resident coating comprising from about 1% to about 70%, by weight of the personal care article, of at least one coating skin treatment active at least partially coating said first porous dissolvable solid substrate, wherein the ratio of the porous dissolvable solid substrate to the surface resident coating is from about 110:1 to about 0.1:1; wherein said skin treatment active comprises zinc pyrithione; wherein said skin treatment active optionally comprises at least one of zinc oxide, zinc hydroxide, zinc carbonate, zinc bicarbonate, and mixtures thereof.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

DETAILED DESCRIPTION OF THE INVENTION

Figure 1:
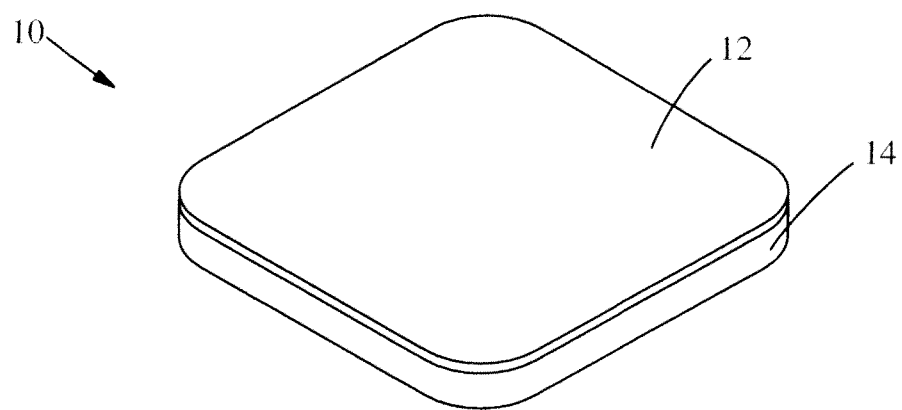
FIG. 1 is a schematic view of a porous dissolvable solid substrate with a surface resident coating comprising a skin treatment active.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

I. DEFINITIONS

As used herein, the term "personal care composition" means a composition that may be applied to mammalian hair and skin without undue undesirable effects.

As used herein, the term "surface resident coating comprising a skin treatment active" refers to a surface resident powder coating comprising the skin treatment active that is adsorbed to at least a portion of the solid/air interface of the porous dissolvable solid substrate. The resulting surface resident coating minimizes the physical interactions between the skin treatment active and the bulk of the dissolvable porous solid both during the manufacture and over the shelf life of the product, and before the personal care article is put in contact with water during consumer use.

As used herein, the term, "surface resident coating" refers to a coating which is adsorbed to at least a portion of the solid/air interface of the porous dissolvable solid substrate.

As used herein, "personal care article" means the porous dissolvable solid substrate comprising a surfactant, water-soluble polymer, and plasticizer, along with the surface resident coating. The personal care article may be referred to herein as "the article."

As used herein, "dissolvable" means that the porous dissolvable solid substrate has a dissolution rate that satisfies the Hand Dissolution Method Test described herein.

As used herein "porous dissolvable solid substrate" means a solid polymer-containing matrix that defines an interconnected network of spaces or cells that contain the gas of the surrounding atmosphere, typically air. The interconnectivity of the structure may be described by a Star Volume, a Structure Model Index (SMI) or a Percent Open Cell Content.

II. PERSONAL CARE ARTICLE

The personal care article of the present invention delivers is capable of delivering new benefits to the consumer from a lathering/cleansing product by enabling the delivery of skin treatment actives which previously had been difficult to incorporate, as many skin treatment actives are generally unstable in the presence of the water traditionally included in personal care products, or have ingredients which are desired to be kept separate until just prior to use by the consumer.

This is achieved by incorporating the skin treatment actives as a surface resident coating on the porous dissolvable solid substrate rather than trying to incorporate the skin treatment active within the porous dissolvable solid substrate during the making process. Any suitable application method can be used to apply the surface resident coating comprising the skin treatment active to the porous dissolvable solid substrate to form a surface resident coating that is adsorbed to at least a portion of the solid/air interface of the porous dissolvable solid substrate. In a one embodiment the surface resident coating comprising the skin treatment active is in the form of a powder coating, which is applied to the surface of the porous dissolvable solid substrate. Traditionally, when skin treatment actives and water are combined together in a composition the skin treatment active does not remain stable (i.e. the skin treatment active either degrades or decomposes or inactivates either during the production process or during the shelf life of the product). Thus when the consumer uses the personal care product the skin treatment active no longer has its intended activity. While this may still occur in the present inventive personal care articles as they are dissolved in water immediately prior to application, the target substrate (i.e. the hair and/or skin) is present when the skin treatment active is first contacted with the water (solvent) and the consumer has a greater opportunity for the skin treatment active to have its intended effect.

A. The Porous Dissolvable Solid Substrate

The porous dissolvable solid substrate comprises a surfactant, a water-soluble polymer, and a plasticizer. The porous dissolvable solid substrate can be prepared such that it can be conveniently and quickly dissolved in the palm of the consumer resulting in a liquid personal care composition. Once dissolved, this personal care composition can be used in a manner similar to conventional liquid personal care compositions, i.e. applied to the scalp and/or hair. The porous dissolvable solid substrate has a maximum Cell Wall Thickness. The porous dissolvable solid substrate has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm. The porous dissolvable solid substrate has a minimum level of interconnectivity between the cells, which is quantified by the Star Volume, the Structure Model Index (SMI), and the Percent Open Cell Content. The porous dissolvable solid substrate has a Star Volume of from about 1 $mm^3$ to about 90 $mm^3$, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$. The porous dissolvable solid substrate has a non-negative Structure Model Index of from about 0.0 to about 3.0, in one embodiment from about 0.5 to about 2.75, and in another embodiment from about 1.0 to about 2.50. The porous dissolvable solid substrate has a Percent Open Cell Content of from about 80% to 100%, in one embodiment from about 85% to about 97.5%, and in another embodiment from about 90% to about 95%. The porous dissolvable solid substrate also has a minimum Specific Surface Area. The porous dissolvable solid substrate has a specific surface area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$. The porous dissolvable solid substrate has a basis weight of from about 125 grams/$m^2$ to about 3,000 grams/$m^2$, in one embodiment from about 300 grams/$m^2$ to about 2,500 grams/$m^2$, in another embodiment from about 400 grams/$m^2$ to about 2,000 grams/$m^2$, in another embodiment from about 500 grams/$m^2$ to about 1,500 grams/$m^2$ and in another embodiment from about 600 grams/$m^2$ to about 1,200 grams/$m^2$, and in another embodiment from about 700 to about 1,000 grams/$m^2$ The porous dissolvable solid substrate has a solid density of from about 0.03 $g/cm^3$ to about 0.40 $g/cm^3$, in one embodiment from about 0.05 $g/cm^3$ to about 0.35 $g/cm^3$, in another embodiment from about 0.08 $g/cm^3$ to about 0.30 $g/cm^3$, in another embodiment from about 0.10 $g/cm^3$ to about 0.25 $g/cm^3$, and in another embodiment from about 0.12 $g/cm^3$ to about 0.20 $g/cm^3$.

In one embodiment, the porous dissolvable solid substrate of present invention is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology.

1. Surfactants in the Porous Dissolvable Substrate

The porous dissolvable solid substrates of the present invention may be lathering or non-lathering under consumer relevant usage instructions. The porous dissolvable substrates include at least one surfactant as a processing aid to generate a stable foam solid prior to drying (solidification) and in the case of a lathering substrate the surfactant may also serve dual functions as a foaming and/or cleansing agent.

a. Lathering Porous Dissolvable Solid Substrates

Lathering porous dissolvable solid substrates for the purposes of lathering and/or cleaning comprise from about 10% to about 75%, in one embodiment from about 30% to about 70%, and in another embodiment from about 40% to about 65% by weight of the personal care article of surfactant; wherein the surfactant comprises one or more surfactants from Group I, wherein Group I includes anionic surfactants that are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Additional suitable Group I and Group II surfactants include those disclosed in U.S. Patent Application No.

61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790.

b. Non-Lathering Porous Dissolvable Solid Substrates

The non-lathering porous dissolvable solid substrates comprise from about 10% to about 75%, in another embodiment from about 15% to about 60%, and in another embodiment from about 20% to about 50% by weight of the personal care article of surfactant; wherein the surfactant comprises one or more of the surfactants described below.

(i) Anionic Surfactants

If the porous dissolvable solid substrate of the present invention is non-lathering, the substrate may comprise a maximum level of 10% (or less than 10%) of anionic surfactants to be used primarily as a process aid in making a stable foam solid. Additional, non-ionic surfactants can be combined with the anionic surfactants to reach a surfactant level which generates a stable foam solid prior to drying.

(ii) Non-Ionic Surfactants

In one embodiment non-ionic surfactants are included as a process aid in making a stable porous dissolvable solid substrate. Suitable nonionic surfactants for use in the present invention include those described in McCutcheon's Detergents and Emulsifiers, North American edition (1986), Allured Publishing Corp., and McCutcheon's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

(iii) Polymeric Surfactants

Polymeric surfactants can also be surfactants to be employed as a process aid in making the porous dissolvable solid substrate of the present invention, either alone or in combination with ionic and/or nonionic surfactants. Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

2. Water-Soluble Polymer ("Polymer Structurant")

The porous dissolvable solid substrate comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L). to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers may be present from about 10% to about 50% by weight of the porous dissolvable solid substrate, in one embodiment from about 15% to about 40% by weight of the porous dissolvable solid substrate, and in yet another embodiment from about 20% to about 30% by weight of the porous dissolvable solid substrate.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous dissolvable solid substrate.

In one embodiment, at least one of the one or more water-soluble polymers is chosen such that about 2% by weight solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

The water-soluble polymer(s) of the present invention can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) in the present invention and are included in U.S. Ser. No. 61/120,786. In one embodiment, water-soluble polymers of the present invention include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methylcelluloses, and carboxymethycelluloses. In another embodiment, water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

In a particular embodiment, the above mentioned water-soluble polymer(s) may be blended with any single starch or combination of starches as a filler material in such an amount as to reduce the overall level of water-soluble polymers required, so long as it helps provide the personal care article with the requisite structure and physical/chemical characteristics as described herein.

In such instances, the combined weight percentage of the water-soluble polymer(s) and starch-based material generally ranges from about 10% to about 50%, in one embodiment from about 15% to about 40%, and in a particular embodiment from about 20% to about 30% by weight relative to the total weight of the porous dissolvable solid substrate. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, *canna, sorghum*, and waxy or high amylase varieties thereof. The starch-based materials may also include native starches that are modified using any modification known in the art, including those described in U.S. Ser. No. 61/120,786.

3. Plasticizer

The porous dissolvable solid substrate of the present invention comprises a water soluble plasticizing agent suitable for use in personal care compositions. In one embodiment, the one or more plasticizers may be present from about 1% to about 30% by weight of the porous dissolvable solid substrate; in another embodiment from about 3% to about 25%; in another embodiment from about 5% to about 20%, and in yet another embodiment, from about 8% to about 15%. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one embodiment, the plasticizers include glycerin or propylene glycol and combinations thereof. European Patent Number EP283165B1 discloses other suitable plasticizers, including glycerol derivatives such as propoxylated glycerol.

4. Optional Ingredients

The porous dissolvable solid substrate may further comprise other optional ingredients that are known for use or otherwise useful in personal care compositions, provided that such optional materials are compatible with the selected essential materials described herein, or do not otherwise unduly impair the performance of the personal care composition.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Examples of such optional ingredients are disclosed in U.S. Ser. No. 12/361,634, 10/392,422 filed Mar. 18, 2003; and US Publication 2003/0215522A1, dated Nov. 20, 2003.

Other optional ingredients include organic solvents, especially water miscible solvents and co-solvents useful as solubilizing agents for polymeric structurants and as drying accelerators. Examples of suitable organic solvents are disclosed in U.S. Ser. No. 12/361,634. Other optional ingredients include: latex or emulsion polymers, thickeners such as water soluble polymers, clays, silicas, ethylene glycol distearate, deposition aids, including coacervate forming components. Additional optional ingredients include anti-dandruff actives including but not limited to zinc pyrithione, selenium sulfide and those actives disclosed in US Publication 2003/0215522A1.

In one embodiment, zinc pyrithione is present in an amount from about 0.05% to about 2%, alternatively from about 0.1% to about 1%, alternatively from about 0.3% to about 0.7%, alternatively at about 0.5% by weight of the personal care article.

B. Surface Resident Coating Comprising a Skin Treatment Active

In one embodiment, the porous dissolvable solid substrates provide a continuous and accessible high surface area "scaffold" (a 3-D network of "struts") for the surface resident coating comprising a skin treatment active to be adsorbed or distributed across creating a high surface area thin coating. This location puts the coating in position to immediately contact water during use.

In one embodiment the ratio of the porous dissolvable solid substrate to the surface resident coating comprising said at least one skin treatment active is from about 110:1 to about 0.1:1, in another embodiment from about 20:1 to about 0.2:1, and in another embodiment from about 10:1 to about 0.3:1, and in yet another embodiment from about 1:1 to about 0.4:1.

The surface resident coating of the present invention comprises one or more skin treatment actives, hereinafter referred to as a coating skin treatment active. Those of skill in the art will understand that the porous dissolvable solid substrate can also include one or more skin treatment actives separate from the at least one surfactant present in the porous dissolvable substrate. In one embodiment, the amount of surface resident coating can be from about 1% to about 70%, by weight of the personal care article, of a coating skin treatment active at least partially coating said first porous dissolvable solid substrate, alternatively from about 10%, or from about 25%, or from about 40%, up to about 60%, or up to about 50% of said skin treatment active.

In one embodiment, the porous dissolvable solid substrate also comprises a skin treatment active (the substrate skin treatment active), which can be the same or a different skin treatment active from said skin treatment active present in the coating (the coating skin treatment active). The level of from the substrate skin treatment active can be from about 0.1% to about 79%, by weight of said personal care article, of said substrate skin treatment active, alternatively from about 1%, or from about 5%, or from about 10%, up to about 65%, up to about 50% of said substrate skin treatment active. In one embodiment, the substrate skin treatment active is one or more anionic surfactants, or a non-ionic surfactant, in addition to the at least one surfactant already present in the substrate.

1. Skin Treatment Actives

In one embodiment, the personal care article is designed for use as a shave preparation. The shave preparation article may be designed for use prior to shaving with any known safety blade or razor commercially available for shaving of skin. In another embodiment, the personal care article is designed for use as a skin care article such as a facial cleanser or hand or body wash article.

In one embodiment, the skin treatment active used in the coating and/or the substrate comprises at least one of the following actives:

a. Moisturizers

Suitable moisturizers, also referred to in the present invention as humectants, include urea, guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g. aloe vera gel), polyhydroxy alcohols (such as sorbitol, glycerol, hexanetriol, propylene glycol, hexylene glycol and the like), polyethylene glycol, sugars and starches, sugar and starch derivatives (e.g. alkoxylated glucose), hyaluronic acid, lactamide monoethanolamine, acetamide monoethanolamine, and mixtures thereof.

b. Emollients

Non-limiting examples of suitable emollients useful in the instant invention are further described in U.S. Pat. No. 4,919,934, Deckner et al. and as described in U.S. Pat. No. 5,665,339 at section D(b)(2). The emollients are used at levels from about 1% to about 10% by weight of the composition. Said emollients include, but are not limited to, volatile and nonvolatile silicone oils, hydrocarbon oils, long chain esters having at least 10 carbon atoms, and mixtures thereof. Suitable emollients are nonvolatile silicone fluids.

Nonvolatile silicone fluids as used herein generally have average viscosities of at least about 1,000 cs, or from about 1,000 to about 2,000,000 cs, or from about 10,000 to about 1,800,000 cs, or from about 100,000 to about 1,500,000 cs at 25° C. Lower viscosity nonvolatile silicone conditioning agents with a minimum viscosity of about 50 cs, can also be used as can volatile cyclic silicones such as, but not limited to octamethylcyclotetrasiloxane, decamethylcyclopentasiloxane, and mixtures thereof.

The hydrocarbon oils include esters with hydrocarbyl chains derived from fatty acids or alcohols (e.g. mono-esters, polyhydric alcohol esters, and di- and tri-carboxylic acid esters). The hydrocarbyl radicals of the fatty esters hereof can also include or have covalently bonded thereto other compatible functionalities, such as amides and alkoxy moieties (e.g. ethoxy or ether linkages). Hydrocarbon oils include saturated or unsaturated cyclic hydrocarbons, straight chain aliphatic hydrocarbons, and branched chain aliphatic hydrocarbons. Straight chain hydrocarbon oils will preferably contain from about 12 to about 19 carbon atoms. Branched chain hydrocarbon oils typically may contain higher numbers of carbon atoms. Examples include paraffin oil, mineral oil, saturated and un-saturated dodecane, saturated and unsaturated tridecane, saturated and unsaturated tetradecane, saturated and unsaturated pentadecane, saturated and unsaturated hexadecane, and mixtures thereof.

Long chain fatty esters include, for example, alkyl and alkenyl esters of fatty acids having aliphatic chains with from about 10 to about 22 C atoms, and alkyl and alkenyl fatty alcohol carboxylic acid esters having an alkyl and/or alkenyl alcohol-derived aliphatic chain with about 10 to about 22 C atoms, and combinations thereof.

c. Vitamins

Vitamins and vitamin derivatives are useful as skin conditioning agents in the present invention particularly in light of the fact that some vitamin and vitamin derivatives are incompatible in water based systems. Vitamins useful in the present invention are generally disclosed in The Condensed Chemical Dictionary, Van Nostrand Reinhold Company, Ninth Edition, pp. 920-921, and Idson, Vitamins and the Skin, Cosmetics and Toiletries Vol. 108, pp. 79-94, December 1993, incorporated herein by reference. A non-limiting example of vitamins that are useful in the present invention is Vitamin E Acetate which is practically water insoluble but is readily soluble in the present invention.

The ingredients used herein, including the pentapeptides and derivatives of pentapeptides actives are stable in the composition and are compatible with each other and with the other skin care actives such as niacinamide, phytantriol, farnesol, bisabolol, and salicylic acid.

Another suitable vitamin for use as a skin treatment active is vitamin B3 compound in a safe and effective amount for use on human skin. Vitamin B3 compounds are particularly useful for regulating skin condition as described in U.S. Pat. No. 6,492,326 to Robinson et al. When vitamin B3 compounds are present in the compositions of the instant invention, the article can contain from about 0.01% to about 50%, or from about 0.1% to about 10%, or from about 0.5% to about 10%, or from about 1% to about 5%, or from about 2% to about 5%, by total weight of the article (including the substrate and coating), of the vitamin B3 compound.

As used herein, "vitamin B3 compound" means a compound having the formula:

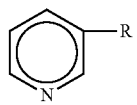

wherein R is —CONH2 (i.e., niacinamide), —COOH (i.e., nicotinic acid) or —CH2OH (i.e., nicotinyl alcohol); derivatives thereof; and salts of any of the foregoing. Exemplary derivatives of the foregoing vitamin B3 compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide. Examples of suitable vitamin B3 compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.). The vitamin compounds may be included as the substantially pure material, or as an extract obtained by suitable physical and/or chemical isolation from natural (e.g., plant) sources.

In one embodiment, where the skin treatment active is a vitamin such as niaciniamide, the level of vitamin can be from about 5% to about 99% by weight of the coating. The coating can also comprise a glycerin/propylene glycol mixture or water.

Another suitable vitamin is vitamin A or a retinoid like compound; non-limiting examples include: retinol, retinal, retinol esters, retinyl propionate, retinoic acid, retinyl palmitate, and mixtures thereof. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. Non-limiting examples of retinoids are provided in U.S. Pat. No. 6,492,326 at section (b) titled Retinoid. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof.

Where a retinoid is included, the retinoid is included at a level of from about 0.005% to or about 2%, more preferably 0.01% to or about 2%, retinoid, by weight of the coating. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%. Where the compositions of the present invention contain both a retinoid and a Vitamin B3 compound, the retinoid is preferably used in the above amounts, and the vitamin B3 compound is preferably used in an amount of from or about 0.1% to or about 10%, more preferably from or about 2% to or about 5%, by total weight of the article.

d. Farnesol

In another embodiment, the skin treatment active comprises a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol. Chemically, farnesol is [2E,6E]-3,7,11-trimethyl-2,6,10-dodecatrien-1-ol and as used herein "farnesol" includes isomers and tautomers of such. In one embodiment, the article contains from about 0.001% to about 50%, by total weight of the article, or from about 0.01% to about 20%, or from about 0.1% to about 15%, or from about 0.1% to about 10%, or from about 0.5% to about 5%, or from about 1% to about 5% of farnesol.

e. Anti-Inflammatory Agents

The skin treatment active of the present invention can include an anti-inflammatory agent. Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

A second class of anti-inflammatory agents which is useful in the compositions includes the nonsteroidal anti-inflammatory agents. The variety of compounds encompassed by this group is well-known to those skilled in the art. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:
1) the oxicams, such as piroxicam, isoxicam, tenoxicam, sudoxicam, and CP-14,304; 2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24.

f. Conditioning Agent

The skin treatment active can also include a conditioning agent, such as a humectants, moisturizer or skin conditioner. Conditioning agents can be at from about 0.01% to about 20%, or from about 0.1% to about 10%, or from about 0.5% to about 7% by total weight of article. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; and mixtures thereof.

g. Inorganic Sunscreen Agents

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

h. Antimicrobial and Antifungal Actives

The skin treatment active of the present invention may contain an antimicrobial or antifungal active. Such actives are capable of destroying microbes, preventing the development of microbes or preventing the pathogenic action of microbes. A safe and effective amount of an antimicrobial or antifungal active may be added to the present article, at from about 0.001% to about 10%, or from about 0.01% to about 5%, or from about 0.05% to about 2%, or from about 0.1% to about 1%, or from about 0.3% to about 0.7%, or at about 0.5% by weight.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Additional actives which can be used as the skin treatment active include: chemical adjuvants (pH buffers, chelants, antioxidants etc.) that can modify the reactivity of one or more other skin treatment actives to either improve the stability profile during the shelf life of the product (in the presence of potential residual moisture levels) or to attenuate or accentuate or otherwise improve the intended activity of the one or more skin treatment actives on the substrate (skin or hair) during consumer usage. In one embodiment, the skin treatment active comprises at least one of desquamatory actives, anti-acne actives, vitamin B3 compounds, retinoids, di-, tri-, and tetra-peptides and derivatives thereof, hydroxy acids, radical scavengers, chelators, anti-inflammatory agents, topical anesthetics, tanning actives, skin lightening agents, anti-cellulite agents, flavonoids, antimicrobial actives, skin healing agents, antifungal actives, farnesol, phytantriol, allantoin, glucosamine, and mixtures thereof. The skin treatment active may also be an anti-cellulite agent. Suitable agents may include, but are not limited to, xanthine compounds (e.g., caffeine, theophylline, theobromine, and aminophylline). The skin treatment active may also be a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof. Another skin treatment active includes: dipropylene glycol; manganese gluconate; peppermint oil; ascorbic acid; calcitrol; glycyrrhetinic acid; pyridoxine; cetyl pyridinium chloride; chamomile; a gelled baby oil comprising mineral oil and kraton polyisobutylene; limonene; linalool; aloe; and mixtures thereof.

Other suitable actives which can be used as skin treatment actives include those listed in the CTFA Cosmetic Ingredient Handbook, Second Edition (1992). The CTFA describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, menthyl lactate, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

The skin treatment active can also include one or more of the surfactants used in the substrate material or a soap. If a surfactant is used, it can be the same or different from any of the surfactants used in the substrate.

The skin treatment active can also include a water soluble lubricant having a molecular weight of from about 90,000 to about 10,000,000 grams/mol. Non-limiting examples of suitable lubricants include a polyethylene oxide ingredient such as PolyOx™ Water Soluble Resins by Dow. Without intending to be bound by theory, it is believed that the degradation of the water soluble lubricants can cause the lubrication benefit to be undesirably decreased. By separating the water soluble lubricant from oxidizing agents as well as minimizing exposure to air, the degradation (from higher mol wt. to a lower mol wt) of the lubricant can be decreased.

i. Heat Generating Agents

The personal care article of the present invention can also be used as a self heating article which can be particularly suitable as a shaving preparation article. Where the article is designed as a self-heating article, the skin treatment actives can be selected from any known actives which are suitable for use in a cosmetic execution and can generate heat suitable for contact to human skin. This embodiment is particularly useful as many heat generating agents may be incompatible to be packaged in one composition or one chamber. The personal care composition of the present invention allows for the separation of any heat generating agents by the consumer just prior to use. Many of these heat generating agents are known and are suitable for use herein.

Non-limiting examples of heat generating actives include combinations of reducing and oxidizing agents; a water sensitive agent, a moisture sensitive agents, and mixtures thereof.

Non-limiting examples of water sensitive agents comprises any at least one of an anhydrous inorganic salt, a zeolite, a glycol, and a mixture thereof. Non-limiting examples of anhydrous inorganic salts including: calcium chloride, magnesium chloride, calcium oxide, magnesium sulphate, aluminium sulphate and combinations thereof. Moisture sensitive agents are those agents which generate heat when in contact with water present in air in the form of moisture. Non-limiting examples of moisture sensitive agents include iron redox systems, such as iron oxide. Where one or more water sensitive agent and/or moisture sensitive agent is used, the agent or agents can be present in one or both of the substrate and coating. In one embodiment, where said agents are present in both substrate and coating, the agents are not the same.

In one embodiment, the personal care article is designed to be a self-heating article comprising a combination of a reducing agent and an oxidizing agent. In one embodiment, at least one of said substrate skin treatment active and said coating skin treatment active comprises a reducing agent. In one embodiment, the substrate comprises the reducing agent and the coating comprises the oxidizing agent. In another embodiment, the substrate comprises the oxidizing agent and the coating comprises the reducing agent. Combinations of more than one oxidizing agent can also be used. Further, combinations of more than one reducing agent can also be used.

Non-limiting examples of suitable oxidizing agents include peroxides, such as hydrogen peroxide (typically added as a 35% solution), benzoylperoxide, peroxomonosulfate, peroxodisulfate, urea hydrogen peroxide, and t-butyl peroxide and mixtures thereof. The oxidizing agent may be included at a level of from about 2% to about 10% by weight of the article. One exemplary oxidizing agent is hydrogen peroxide (at about 4% to about 6% $H_2O_2$ active).

Examples of suitable reducing agents for use in the reducing component are those that will react with the oxidizing agent when the substrate and the coating dissolve and come into intimate contact with one another. Suitable reducing agents should also be safe for use on human skin in the amounts used in the formulation. The reducing agent may include, for example, thiosulfate and sulfite compounds, such as sodium sulfite, sodium thiosulfate (e.g., sodium thiosulfate pentahydrate), ammonium thiosulfate, potassium thiosulfate, thiourea and mixtures thereof. Other suitable reducing agents include compounds with a thiourea backbone, such as 1,5-diethyl-2-thiobarbituric acid or its derivatives, or ascorbic acid. Mixtures of the above reducing agents, and other suitable reducing agents, may also be used. In some embodiments, the personal care article includes from about 2% to about 10%, preferably from about 3% to about 8%, of a reducing agent by weight. Other ingredients such as pepper oils, such as black pepper essential oil, capsaicin and benzyl nicotinate can also be used as the reducing agent.

The oxidizing agent and reducing agent are generally included in approximately stoichiometric proportions, based on the redox reaction that will occur. The predominant redox reaction of hydrogen peroxide with sodium thiosulfate is as follows:

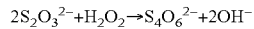

In the presence of an adequate amount of an effective catalyst, the reaction is as follows:

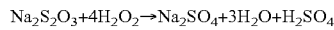

Preferably, the maximum temperature obtained by the shave foam during the reaction is from about 30° C. to about 60° C., and this temperature is reached from about 1 seconds to about 45 seconds after the two components are mixed (this is the temperature the dissolved article reaches when the oxidant agent and the reductant agent are mixed in a beaker in stoichiometric amounts, the desired temperature on the skin would typically from about 28° C. to about 45° C.). When the oxidizing agents and reducing agents described above are used, the dissolved personal care article generally includes from about 2% to about 10% of the oxidizing agent and from about 2% to about 10% of the reducing agent, in approximately stoichiometric proportions.

To obtain the heat profile described above, it may be advantageous to include a catalyst in the shave foam composition. The catalyst is selected to catalyze the exothermic reaction, without deleterious effects on the skin or on the properties of the shave foam. The catalyst is generally included in the reductant component of the shave foam composition. Suitable catalysts for the exothermic reaction described above include sodium molybdate (e.g., sodium molybdate dihydrate), potassium molybdate, ammonium molybdate, sodium tungstate, potassium tungstate, and mixtures thereof. The article generally includes 0.1% to about 1.5%, or about 0.2% to about 1.0%, of the catalyst.

If the exothermic reaction generates an acid, as the reaction of the oxidizing and reducing agents discussed above will generally do, it is preferred that the composition (e.g., the reductant component) also include a neutralizing agent (a neutralizer). The neutralizing agent is selected and provided in a sufficient amount to neutralize enough of the acid so that exothermic reaction is complete and the shave foam composition will not irritate the user's skin. Preferably, substantially all of the acid is neutralized. Suitable neutralizing agents include, for example, triethanolamine, oxides (e.g., metal oxides), hydroxides (e.g., metal hydroxides), and metal carbonates, such as carbonates of alkaline metals (e.g., sodium, potassium), alkaline-earth metals (e.g., magnesium, barium), or transition metals (e.g., zinc). For example, the neutralizing agent may include calcium oxide, potassium hydroxide, sodium hydroxide, potassium bicarbonate, sodium bicarbonate or aluminum hydroxycarbonate. In some embodiments, the article (preferably the component comprising the reductant agent) can include from about 0.5% to about 10% of such a neutralizer by weight of the article. For example, one of the substrate or the coating can include about 1% calcium oxide or about 7% triethanolamine. Additional examples of self heating compositions include those disclosed in U.S. Pat. Nos. 3,772,203; 4,439,416.

2. Color Indicators

The surface resident coatings of the present invention may also comprise color indicators. Such color indicators can be present in an amount sufficient to result in a visual color change when the indicator is contacted with water. The term "visual color change" refers to a color change that can be detected by the human eye, either alone, or with the aid of an energy source such as a black light. The color indicators of the present invention can include, but are not limited to, those selected from the group consisting of pH indicators, photoactive pigments, thermochromatic pigments, and combinations thereof. In one embodiment the color changes from red to blue, in another embodiment from red to yellow, and in another embodiment from yellow to green, and in yet another embodiment from blue to red, and in yet another embodiment from colorless to color, and in yet another embodiment from color to colorless.

In one embodiment the color change is a pH sensitive color changing component. The color indicators can be selected from the group consisting of bromocresol green, phenolphthalein, σ-cresolphthalein, thymolphthalein, coumarin, 2,3-dioxyxanthone, coumeric acid, 6,8-dinitro-2,4(1H) quinazolinedione, ethyl-bis(2,4-dimethylphenyl)ethanoate, and combinations thereof.

3. Optional Ingredients

Optional ingredients may also be included in the surface resident coatings of the present invention. Optional ingredients include non oxidative hair dyes i.e. direct dyes which may be used alone or in combination with the above described oxidative dyes. Suitable direct dyes include azo or anthraquinone dyes and nitro derivatives of the benzene series and or melanin precursors and mixtures thereof. Such direct dyes are particularly useful to deliver shade modification or highlights. Particularly embodiments are Basic Red 51, Basic Orange 31, Basic Yellow 87 and mixtures thereof.

The surface resident coatings of the present invention may also include a non-hygroscopic solvent to mitigate moisture from the environment precipitating a premature reaction with or between the skin treatment active or actives, before these chemical constituents come into contact with liquids. The term non-hygroscopic solvent is defined herein as any compound that does not take up moisture from the environment. In some embodiments, the non-hygroscopic solvent is capable of dissolving or dispersing at least a small amount of one or more other substances. Such non-hygroscopic solvents include, but are not limited to diethyl phthalate, isopropyl myristate, isopropyl palmitate and at least some species of ester solvents, such as dioctyl adipate and butyl stearate. In other embodiments, the non-hygroscopic solvent may be non-polar (aprotic).

The surface resident coatings of the present invention may encompass skin treatment actives in particulate form that are at least partially coated with anhydrous oils and/or waxes. Examples of waxes include, but are not limited to, natural waxes and derivatives of such waxes (derived from plants and animals) and synthetic waxes.

The surface resident coatings of the present invention may also include water absorbents such as Vermiculite as an inexpensive water reservoir. Vermiculite is an aluminum-iron magnesium silicate. In certain systems salts such as sodium chloride may be employed to further assist the reaction. Cosmetic product dispensers are preferred which seal the product from the atmosphere during storage periods.

Additional skin treatment actives can also be used. Non-limiting examples of additional suitable skin treatment actives are included in U.S. 2003/0082219 in Section I (in particular hexamidine, zinc oxide, and niacinamide) and U.S. Pat. No. 5,665,339 at section D—Cosmetically active ingredients, such as coolants, skin conditioning agents, sunscreens and pigments, and medicaments.

C. Method of Applying the Surface Resident Coating

The surface resident coating of the present invention is applied to the porous dissolvable solid substrate. In one embodiment, the surface resident coating is in the form of a fine powder. As seen in FIG. 1, in certain embodiments of the present invention, the personal care article 10 contains a surface resident coating 12 that is located on at least a portion of the surface of the porous dissolvable solid substrate 14. It will be appreciated that the surface resident coating 12 may not always be adjacent to the porous dissolvable solid substrate 14. In certain embodiments, the surface resident coating 12 may permeate the porous dissolvable solid substrate 14 in whole or in part.

Alternatively, the surface resident coating can be included (e.g., sandwiched or encased) within the personal care article or parts thereof. Such a surface resident coating can be sprayed, dusted, sprinkled, coated, surface-printed (e.g., in the shape of a desired adornment, decoration, or pattern), poured on, injected into the interior, dipped, or by any other suitable means, such as by use of a depositor, sifter, or powder bed.

Those of skill in the art should understand that the coating can be applied as a powder coating or can be a fluid coating which is then dried. For instance, where the coating is a fluid coating, the coating can be sprayed, spread, dropped, printed, sandwiched between different articles or different portions of the same article, layered, injected, rolled on, or dipped. The coating can be applied over portions or entire regions of the article's exterior surface, and can be applied in a manner to adorn, decorate, form a logo, design, etc.

Figure 3A:
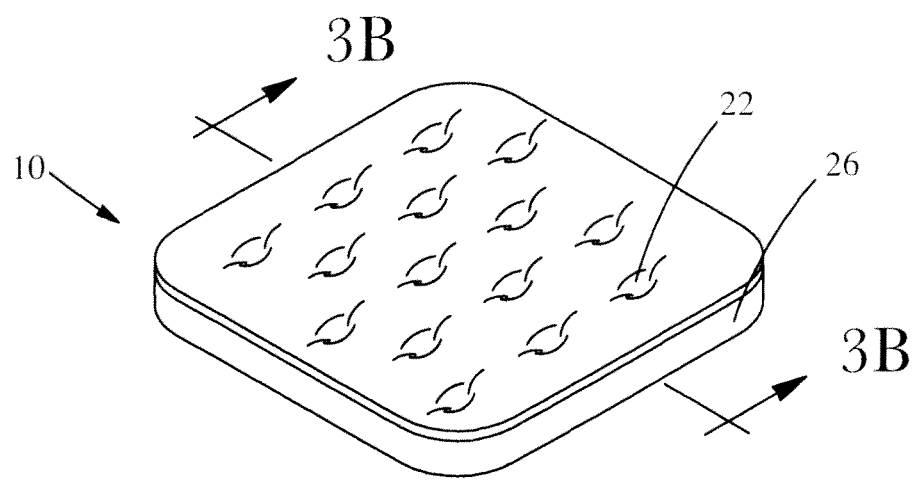
FIGS. 3A and 3B are schematic views of a dimpled porous dissolvable solid substrate with a surface resident coating comprising a skin treatment active inside the dimples.
Figure 3B:
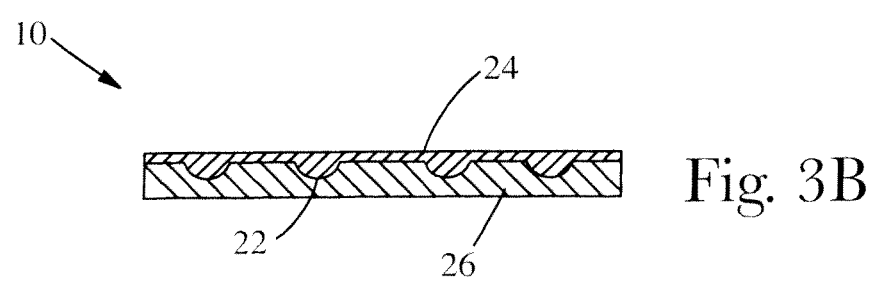
Figure 4:
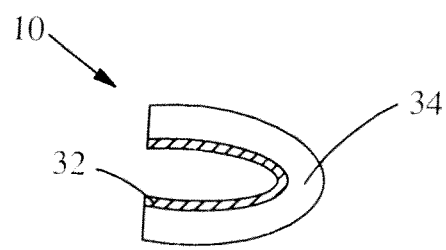
FIG. 4 is a schematic view of a porous dissolvable solid substrate that is folded over to enclose a surface resident coating comprising a skin treatment active.

In the embodiments depicted by FIGS. 3A, 3B, and 4, the personal care article 10 contains a surface resident coating that can be situated below the surface of the porous dissolvable solid substrate. As seen in FIG. 3B which is a cross sectional view of the personal care article 10, the surface resident coating 24 is located within the dimples 22 of the porous dissolvable solid substrate 26.

Figure 2:
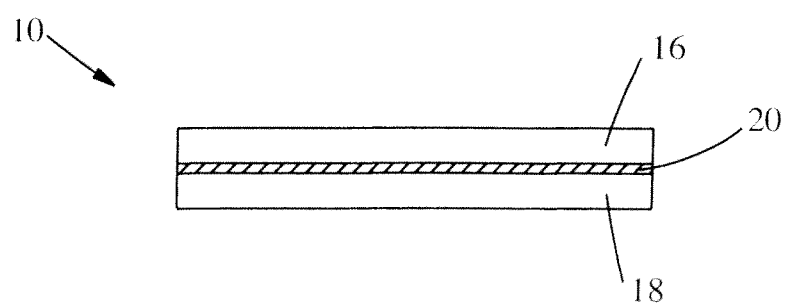
FIG. 2 is a schematic view of two porous dissolvable solid substrates with a surface resident coating comprising a skin treatment active.

Referring now to FIG. 2, in certain embodiments the powder is sandwiched between two porous dissolvable solid substrate which are then joined together (e.g., via sealing the adjoining surfaces or edges with a thin layer of water and/or plasticizer so as to not substantially dissolve the porous dissolvable solid substrate and applied pressure to induce adhesion). In this embodiment, the personal care article 10 comprises two porous dissolvable solid substrates 16, 18 in between which a surface resident coating 20 is located. In another embodiment, the substrate is at least partially coated with a first coating and a second coating, wherein the multiple coatings can be applied to separate areas of the substrate, such as separate sides of the substrate, or the multiple coatings can be applied one over the other.

Alternatively, in certain embodiments, the powder may be on one personal care article which is folded over to form a pouch, encasing the powder. As depicted in FIG. 4, the personal care article 10 comprises a surface resident coating 32 that is enclosed within a folded porous dissolvable solid substrate 34.

The personal care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the personal care article, for example the personal care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the personal care article can be perforated with holes or channels penetrating into or through the porous solid.

III. PRODUCT FORM OF THE PERSONAL CARE ARTICLE

The personal care article can be produced in any of a variety of product forms, including porous dissolvable solid substrates along with the surface resident coating comprising the skin treatment actives used alone or in combination with other personal care components. Regardless of the product form, the product form embodiments contemplated herein include the selected and defined personal care article that comprises a combination of a porous dissolvable solid substrate and a surface resident coating comprising a skin treatment active.

In one embodiment, the personal care article is in the form of one or more flat sheets or pads of an adequate size to be able to be handled easily by the user. In one embodiment, the invention comprises two or more porous dissolvable substrates, which can be at least partially laminated on one another. In one embodiment, the substrates can be at least partially separated by the coating. In another embodiment, one or more coatings can be applied over the one or multiple substrates. It may have a square, rectangle or disc shape or any other suitable shape. The pads can also be in the form of a continuous strip including delivered on a tape-like roll dispenser with individual portions dispensed via perforations and or a cutting mechanism. Alternatively, the personal care articles are in the form of one or more cylindrical objects, spherical objects, tubular objects or any other shaped object.

The personal care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the personal care article, for example the personal care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the personal care article can be perforated with holes or channels penetrating into or through the porous solid.

IV. METHOD OF MANUFACTURE

The personal care article can be prepared by the process comprising: (1) Preparing a processing mixture comprising surfactant(s), dissolved polymer structurant, and plasticizer; (2) Aerating the processing mixture by introducing a gas into the processing mixture to form an aerated wet mixture; (3) Forming the aerated wet mixture into one or more desired shapes; (4) Drying the aerated wet mixture to form a porous dissolvable solid substrate; and (5) Applying the surface resident coating comprising a skin treatment active in powdered form to the porous dissolvable solid substrate.

A. Preparation of Processing Mixture

The processing mixture is generally prepared by dissolving the polymer structurant in the presence of water, plasticizer, surfactant and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including step-wise processing via pre-mix portions of any combination of ingredients.

The processing mixtures of the present invention comprise: from about 15% to about 60% solids, in one embodiment from about 20% to about 55% solids, in another embodiment from about 25% to about 50% solids, and in yet another embodiment from about 30% to about 45% solids by weight of the processing mixture before drying; and have a viscosity of from about 2,500 cps to about 150,000 cps, in one embodiment from about 5,000 cps to about 100,000 cps, in another embodiment from about 7,500 cps to about 75,000 cps, and in still another embodiment from about 10,000 cps to about 60,000 cps.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500Rheometer with 4.0 cm diameter parallel plate and 1,200 micron gap at a shear rate of 1.0 reciprocal seconds for a period of 30 seconds at 23° C.

B. Aeration of Processing Mixture

The aeration of the processing mixture is accomplished by introducing a gas into the mixture. In one embodiment this is done by mechanical mixing energy. In another embodiment this may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the personal care article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Aeration can also be accomplished with chemical foaming agents by in-situ gas formation (via chemical reaction of one or more ingredients, including formation of carbon dioxide ($CO_2$ (g)) by an effervescent system. An additional possibility is aeration via volatile blowing agents such as low boiling hydrocarbons or alcohols including, but not limited to, isopentane, pentane, isobutene, ethanol etc.

In one embodiment, the pre-mixture is pre-heated immediately prior to the aeration process at above ambient temperature but below any temperatures that would cause undesirable degradation of any of the components. In one embodiment, the pre-mixture is kept at above about 40° C. and below about 99° C., in another embodiment above about 50° C. and below about 95° C., in another embodiment above about 60° C. and below about 90° C. In one embodiment, when the viscosity at ambient temperature of the pre-mix is from about 20,000 cps to about 150,000 cps, the optional continuous heating should be utilized before the aeration step. In another embodiment, additional heat is applied during the aeration process to try and maintain an elevated temperature during the aeration. This can be accomplished via conductive heating from one or more surfaces, injection of steam, a surrounding hot water bath, or other processing means.

In one embodiment the wet density range of the aerated pre-mixture ranges from about 0.12 $g/cm^3$ to about 0.50 $g/cm^3$, in another embodiment from about 0.15 $g/cm^3$ to about 0.45 $g/cm^3$, in another embodiment from about 0.20 $g/cm^3$ to about 0.40 $g/cm^3$, and in yet another embodiment from about 0.25 $g/cm^3$ to about 0.35 $g/cm^3$.

C. Forming the Aerated Wet Processing Mixture

The forming of the aerated wet processing mixture may be accomplished by any suitable means to form the mixture in a desired shape or shapes including, but not limited to (i) depositing the aerated mixture to moulds of the desired shape and size comprising a non-interacting and non-stick surface including aluminium, Teflon, metal, HDPE, polycarbonate, neoprene, rubber, LDPE, glass and the like; (ii) depositing the aerated mixture into cavities imprinted in dry granular starch contained in a shallow tray, otherwise known as starch moulding forming technique; and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. Drying the Aerated Wet Processing Mixture into a Porous Dissolvable Solid Substrate The drying of the formed aerated wet processing mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers, and combinations thereof. Any suitable drying means that does not comprise freeze-drying can be used.

The drying temperature may range from about 40° C. to about 200° C. In one embodiment, the drying environment is heated to a temperature between 100° C. and 150° C. In one embodiment, the drying temperature is between 105° C. and 145° C. In another embodiment, the drying temperature is between 110° C. and 140° C. In a further embodiment, the drying temperature is between 115° C. and 135° C.

Other suitable drying environments include "volumetric heating" techniques using high frequency electromagnetic fields such as Microwave Drying and Radio Frequency (RF) Drying. With these techniques, the energy is transferred electromagnetically through the aerated wet pre-mixture rather than by conduction or convection.

Optional ingredients may be imparted during any of the above described four processing steps or even after the drying process.

E. Preparing the Surface Resident Coating Comprising the Skin Treatment Active

The preparation of the surface resident coating comprising the skin treatment active may include any suitable mechanical, chemical, or otherwise means to produce a particulate composition comprising the skin treatment active including any optional materials as described herein, or a dried coating from a fluid.

Where the article has a particulate coating, the particle size is known to have a direct effect on the potential reactive surface area of the skin treatment actives and thereby has a substantial effect on how fast the skin treatment active delivers the intended beneficial effect upon dilution with water. In this sense, the skin treatment actives with smaller particle sizes tend to give a faster and shorter lived effect, whereas the skin treatment actives with larger particle sizes tend to give a slower and longer lived effect. In one embodiment the surface resident coatings of the present invention may have a particle size from about 1 μm to about 200 μm, in another embodiment from about 2 μm to about 100 μm, and in yet another embodiment from about 3 μm to about 50 μm. In one embodiment, the powder coating is solidified by cross-linking the particles with an inorganic salt, such as a calcium salt or an aluminium salt.

In some embodiments, it is helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling etc. The resulting powder may also be blended with other inert powders, either of inert materials or other powder-active complexes, and including water absorbing powders as described herein.

In one embodiment, the skin treatment actives may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the skin treatment active particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the skin treatment actives, of the surface resident coating composition and with subsequent particle size reduction as per the procedure described above.

Where the coating is applied to the substrate as a fluid (such as by as a spray, a gel, or a cream coating), the fluid can be prepared prior to application onto the substrate or the fluid ingredients can be separately applied onto the substrate such as by two or more spray feed steams spraying separate components of the fluid onto the substrate.

F. Combining Surface Resident Coating Comprising the Skin Treatment Actives with the Porous Dissolvable Solid Substrate Any suitable application method can be used to apply the surface resident coating comprising skin treatment active to the personal care article such that it forms a part of the personal care article. For instance, the porous dissolvable solid substrate can have a tacky surface by drying the porous dissolvable solid substrate's surface to a specific water content before application of powder to facilitate the adherence of the surface resident coating comprising the skin treatment actives to the porous solid. In one embodiment, the porous dissolvable solid substrate is dried to a moisture content of from about 0.1% to about 25%, in one embodiment from about 3% to about 25%, in another embodiment from about 5% to about 20% and in yet another embodiment from about 7% to about 15%. Alternatively, a previously dried dissolvable porous solid substrate's surface can be made to reversibly absorb a desired level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In one embodiment, the step of at least partially drying the particulate coating is by cross linking said powder with an inorganic salt further comprises at least one of: gravimetric drying said coating in a hot air oven; filtration drying said coating; storing in controlled temperature chambers at from about 35 C to about 40 C for a time of from about 2 to about 72 hours, and a combination thereof.

In another embodiment, the porous dissolvable solid substrate is placed in a bag, tray, belt, or drum containing or otherwise exposed to the powder and agitated, rolled, brushed, vibrated or shaken to apply and distribute the powder, either in a batch or continuous production manner. Other powder application methods may include powder sifters, electrostatic coating, tribo charging, fluidized beds, powder coating guns, corona guns, tumblers, electrostatic fluidized beds, electrostatic magnetic brushes, and/or powder spray booths. The surface resident coating comprising the skin treatment active can be applied over portions or entire regions of the porous dissolvable solid substrate's exterior surface, and can be applied in a manner to adorn, decorate, form a logo, design, etc.

Where the coating is applied to the substrate in a fluid and then subsequently solidified by at least partially dried to the point it will stay on the exterior of the substrate, it is preferable that if water is present in the fluid that the water is not sufficient to cause the substrate to undesirable dissolve. Other non-water solvents, such as organic solvents which do not cause the substrate to dissolve may be used. Those of skill in the art will understand that the combination of water content in the coating material as well as temperature and pressure can be used to minimize any dissolution of the substrate during the coating process. In one embodiment, where a fluid coating is used, the fluid coating comprises less than about 70% water prior to drying.

The step of drying said coating can be done at ambient temperatures or at elevated temperatures. Non-limiting examples of suitable coatings include gel coatings or cream coatings which can be dried to form the solid coating. The coatings can be applied by dip coating the substrate in a dipping bath or by using rollers to apply the fluids onto the substrates. The fluid can also be sprayed onto the substrate.

V. TEST METHODS

A. Dissolution Rate

The personal care article of present invention has a Dissolution Rate that allows the personal care article to rapidly disintegrate during use application with water. The Dissolution Rate of the personal care article is determined in accordance with the methodology described below.

Hand Dissolution Method: 0.5 to 1.5 g (approximately 10 to 20 square centimeters if in a 3 to 10 mm thick sheet/pad form) of the personal care article (as described in the examples herein) is placed in the palm of the hand while wearing nitrile gloves. 7.5 cm$^3$ of warm tap water (from about 30° C. to about 35° C.) is quickly applied to the personal care composition via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum. For the latter scenario, the weight of the undissolved material is also reported.

The personal care articles of the present invention have a hand dissolution value of from about 1 to about 30 strokes, in one embodiment from about 2 to about 25 strokes, in another embodiment from about 3 to about 20 strokes, and in still another embodiment from about 4 to about 15 strokes.

B. Thickness

The thickness of the personal care article and/or the porous dissolvable solid substrate is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 μm/cm$^2$).

The thickness of the personal care article and/or the porous dissolvable solid substrate is measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

C. Basis Weight

The Basis Weight of the personal care article and/or the porous dissolvable solid substrate is calculated as the weight of the personal care article and/or the porous dissolvable solid substrate per area of the selected personal care article and/or the porous dissolvable solid substrate (grams/m$^2$). The area is calculated as the projected area onto a flat surface perpendicular to the outer edges of the personal care article and/or the porous dissolvable solid substrate. For a flat object, the area is thus computed based on the area enclosed within the outer perimeter of the sample. For a spherical object, the area is thus computed based on the average diameter as 3.14× (diameter/2)$^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side.

D. Solid Density

The porous dissolvable solid substrate of the personal care compositions described herein can be characterized in terms of a solid density determination.

The solid density of the porous dissolvable solid substrate can be determined by dividing the weight of the solid by the known volume of the solid. The latter can be determined by a number of techniques including producing the solid within a mold of known x-y dimensions and measuring the resulting thickness to account for any shrinkage or expansion during the drying process. The solid can also be cut to known x-y dimensions, i.e., by using a circular or square cutting die of known diameter or dimensions and then by measuring the thickness. Alternatively, in the instances where there are not any significant thickness variations, the density can be calculated by the equation:

Calculated Density=Basis Weight of porous solid/
(Average porous Solid Thickness×1,000).

E. Cell Inter-Connectivity

The personal care article and/or the porous dissolvable solid substrate of the present invention have a high degree of cell inter-connectivity, i.e., are predominantly open-celled solid foams as opposed to being predominantly closed-cell solid foams. The cell inter-connectivity can be assessed by light microscopy, scanning electron microscopy, micro computed tomography imaging parameters (Star Volume and SMI Index), gas pyncnometry parameters (% Open Cells), or other suitable methodology.

A qualitative method of determining cell inter-connectivity is via light microscopy. This is performed by cutting a 2-3 mm wide sliver of the personal care article and/or the porous dissolvable solid substrate in the z-direction using scissors or a sharp blade, measured across the normal x-y largest surface, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus Olympus America Inc., Center Valley, Pa. The open-celled personal care article and/or the porous dissolvable solid substrate of the present invention can easily be identified by examining the inner portion of the cross-sectional area which comprises a predominantly three dimensional network of struts with open void spaces surrounding the struts that are inter-connected to one another including in the third dimension through the depth of the cross-section. In contrast, the inner cross-section of a closed-cell foam appears as discrete bubbles that are cut across and then only being inter-connected at the cross-sectional surface in two dimensions by virtue of the cutting process employed to generate the exposed cross-sectional area.

Another means to determine the cell interconnectivity is via the Star Volume and the Structure Model Index. Disk-like samples, approximately 4 cm in diameter and 3 to 7 mm high, are scanned using a micro computed tomography system (µCT80, SN 06071200, Scanco Medical AG). Each sample is imaged while sitting flat on the bottom of a cylindrical tube. Image acquisition parameters are 45 kVp, 177 µA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 µm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 - \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334.:

$$StarVolume = \frac{4}{3}\pi \cdot \frac{\sum dist^3}{N}$$

where "dist" is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

F. Cell Wall Thickness

The Cell Wall Thickness of the personal care article and/or the porous dissolvable solid substrate is computed from the scanned images via a micro computed tomography system (µCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

G. Specific Surface Area

The Specific Surface Area of the personal care article and/or the porous dissolvable solid substrate is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately $1/300$ that of nitrogen at liquid nitrogen temperature (krypton: 2.5 torr; nitrogen: 760 torr). Therefore, compared to nitrogen, there is in the free space above the sample about $1/300$ the number of krypton molecules present at the same relative pressure. Since about the same number of krypton and nitrogen molecules are required to form a monolayer, this number represents a far greater proportion of the quantity dosed than in the case of nitrogen. These measurements can be conducted by Micromeretics Analytical Services, Inc. (One Micromeritics Dr, Suite 200, Norcross, Ga. 30093). More information on this technique is available on the Micromeritics Analytical Services web sites (www.particletesting.com or www.micromeritics.com), or published in a book, "Analytical Methods in Fine particle Technology", by Clyde Orr and Paul Webb.

H. Evaluation of Surface Resident Coating

The presence of a surface resident coating comprising a skin treatment active of the present invention can be determined by a number of techniques. For detection of a particulate or powder coating, the surface of application as well as the cross-sections perpendicular to the larger surfaces of the porous dissolvable solid substrate can be examined by microscopic techniques. These microscopic techniques may include light microscopy and scanning electron microscopy (SEM). The light microscopy may include but are not necessarily limited to bright field, dark field, or confocal microscopy techniques. Other techniques for mapping unique elements such as silicon or distinctive functional groups such as quaternary ammonium groups on the cross-sectional surface include: time of flight secondary ion mass spectroscopy (ToF-SIMS), or infrared microscopy.

Potential methods for looking at the distribution of particles from the surface to the interior of the porous dissolvable solid substrate without sectioning the samples include: micro-Computed Tomography (micro-CT), Magnetic Resonance Imaging (MRI), Acoustic Imaging, Confocal Fluorescence Microscopy, Confocal Raman Spectroscopy, and Confocal Infrared Reflectance Spectroscopy.

The determination of surface-resident coating particles on cross-sectioned porous dissolvable solid substrate can be performed by comparing the distribution of the particles across the cut cross-section of the porous solid. Specifically, the surface resident coating particles should be present at the original solid/air interfaces, but not within the exposed cross sectioned interior of the solid cell walls as can be ascertained by analyzing the exposed freshly cut cross-sectional interiors of the solid. It should be noted that some contamination of the freshly cut cross-sectional solid cell wall interiors may occur as a consequence of the cutting process of the porous solid. However, the preponderance (in one embodiment, from about 50% to about 100%) of the surface resident coating particle distribution will occur at the original solid/air interfaces and not within the exposed cut cross-sectional interiors of the cell walls.

It should also be noted that the surface resident coating particles of the present invention generally do not spread uniformly across all exposed solid/air interfaces. Rather, it has been found that the surface resident coatings of the present invention typically spread, from the point of coating application, into cavities down to about 0.5 to about 3.0 mm according to gravity. Accordingly, the determination of surface resident particles of cosmetic actives of the present invention (as described above), should be conducted across many different cross sections from top-to-bottom and from edge-to-edge of the porous solid. If present, the surface resident cosmetic active particle will generally be within the regional vicinity (to within about 0.5 to about 3.0 mm from the surface) of the surface to where the coating was first applied.

IV. METHODS OF USE

The compositions of the present invention may be used for treating mammalian keratinous tissue such as face and neck, armpits, and/or legs, and provide rapid rinse-ability. Where the personal care article is a shave preparation article, the article can be designed for application to any portion of the body where hair removal is desired. The present invention also provides for methods of use comprising: contacting a personal care article of the present invention with water to allow said personal care article to at least partially dissolve; applying said at least partially dissolved personal care article to a surface to form a prepared surface; shaving said prepared surface with a razor. In one embodiment, the user is directed to wait a certain amount of time between applying the at least partially dissolved shave on the skin prior to shaving. Without intending to be bound by theory, it is believed that waiting allows the skin treatment actives and water to absorb onto the skin and into any hairs making for a more enjoyable shave experience and reducing the chance of skin irritation. In one embodiment, the user is instructed to wait from about 5 seconds to about 240 seconds, or from about 20 seconds to about 120 seconds, or from about 30 seconds to about 60 seconds. The user can also be instructed on the temperature of water to be used to trigger the dissolution of the article (in one embodiment warm to room temperature water is used) as well as the temperature of water to be used on the face after a shave (in one embodiment warm or room temp water is used to wash off any excess composition, then cold or room temp water is used afterwards). Where the shave prep active is a depilatory, the step of shaving may not be necessary. These steps can be repeated as many times as desired to achieve the desired treatment benefit.

Where the article is designed for use as a skin care article, such as a facial cleanser or body wash, the steps of use can include contacting said article with water to at least partially dissolve the article, preferably entirely dissolve the article, and then the at least partially dissolved composition can be contacted onto skin for scrubbing and washing. The water can be warm or cool water, where warm water would likely accelerate the speed of dissolution.

Note that any actives and/or compositions disclosed herein can be used in and/or with the articles, and in particular the household care articles, disclosed in the following U.S. patent applications, including any publications claiming priority thereto: U.S. Ser. No. 12/831,618; U.S. Ser. No. 12/847,093; U.S. 61/229,990; U.S. 61/229,996; U.S. Ser. No. 12/847,110; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care article comprising:
   a.) a first porous dissolvable solid substrate comprising:
      i. from about 10% to about 75%, by weight of the first porous dissolvable solid substrate, of at least one surfactant;
      ii. from about 10% to about 50%, by weight of the first porous dissolvable solid substrate, of a water-soluble polymer;
      iii. from about 1% to about 30%, by weight of the first porous dissolvable solid substrate, of a plasticizer; and
   b.) a surface resident coating comprising from about 1% to about 70%, by weight of the personal care article, of at least one coating skin treatment active at least partially coating said first porous dissolvable solid substrate,
      wherein the ratio of the porous dissolvable solid substrate to the surface resident coating is from about 110:1 to about 0.1:1; and
   wherein said coating skin treatment active comprises zinc pyrithione.

2. The personal care article of claim 1, wherein the coating skin treatment active further comprises at least one of: a moisturizer; an emollient; a vitamin; a shave prep oil; a depilatory; a petrolatum; a niacinamide; a retinoid; a farnesol; an anti-inflammatory agent; a conditioning active; an inorganic sunscreen active; an antimicrobial active; menthol; menthyl lactate; caffeine; an anti-cellulite agent; a topical anesthetic; dipropylene glycol; manganese gluconate; peppermint oil; ascorbic acid; calcitrol; glycyrrhetinic acid; pyridoxine; cetyl pyridinium chloride; chamomile; a gelled baby oil comprising mineral oil and kraton polyisobutylene; limonene; linalool; aloe; and mixtures thereof.

3. The personal care article of claim 1, wherein said first porous dissolvable solid substrate further comprises from about 0.1% to about 79% of a substrate skin treatment active.

4. The personal car article of claim 3, wherein the substrate skin treatment active and the coating skin treatment active are different.

5. The personal care article of claim 3, wherein the substrate skin treatment active is an anionic surfactant.

6. The personal care article of claim 3, wherein at least one of said substrate skin treatment active and said coating skin treatment active comprises a reducing agent.

7. The personal care article of claim 6, wherein the reducing agent comprises a thiosulfate, a sulfite compounds, pepper oil, capsaicin, benzyl nicotinate, or a mixture thereof.

8. The personal care article of claim 6, wherein an oxidizing agent is included in the substrate skin treatment active or the coating skin treatment active which does not include the reducing agent.

9. The personal care article of claim 8, wherein said oxidizing agent comprises a peroxide.

10. The personal care article of claim 3, wherein at least one of said substrate skin treatment active and said coating skin treatment active comprises an oxidizing agent.

11. The personal care article of claim 3, wherein at least one of said substrate skin treatment active and said coating skin treatment active comprises a heat generating active comprising a water sensitive agent, a moisture sensitive agent, or a mixture thereof.

12. The personal care article of claim 11, wherein said water sensitive agent comprises an anhydrous inorganic salt, a zeolite, a glycol, and a mixture thereof.

13. The personal care article of claim 3, wherein at least one of said coating skin treatment active and said substrate skin treatment active comprises a water soluble lubricant having a molecular weight of from about 90,000 to about 10,000,000 grams/mol.

14. The personal care article of claim 1, further comprising a second porous dissolvable solid substrate at least partially laminated to said first porous dissolvable solid substrate.

15. The personal care article of claim 14, wherein the first and second porous dissolvable solid substrates are at least partially separated by said surface resident coating.

16. The personal care article of claim 1, wherein said surface resident coating further comprises at least one surfactant.

17. A method of treating a surface comprising:
contacting a personal care article of claim 1 with water to allow said personal care article to at least partially dissolve;
applying said at least partially dissolved personal care article to a surface to form a prepared surface; and
optionally shaving said prepared surface with a razor.

18. A personal care article comprising:
a.) a first porous dissolvable solid substrate comprising:
   iv. from about 10% to about 75%, by weight of the first porous dissolvable solid substrate, of at least one surfactant;
   v. from about 10% to about 50%, by weight of the first porous dissolvable solid substrate, of a water-soluble polymer;
   vi. from about 1% to about 30%, by weight of the first porous dissolvable solid substrate, of a plasticizer;
   vii. from about 0.05% to about 2%, by weight of zinc pyrithione;
   viii. optionally from about 0.05% to about 5% by weight of at least one of a metal oxide, metal hydroxide, metal carbonate, metal bicarbonate, and mixtures thereof; and
b.) optionally, a surface resident coating comprising from about 1% to about 70%, by weight of the personal care article, of at least one coating skin treatment active at least partially coating said first porous dissolvable solid substrate, wherein the ratio of the porous dissolvable solid substrate to the surface resident coating is from about 110:1 to about 0.1:1.

19. The personal care article of claim 18, wherein the metal oxide is zinc oxide, the metal hydroxide is zinc hydroxide, the metal carbonate is zinc carbonate, and the metal bicarbonate is zinc bicarbonate.

* * * * *